(12) United States Patent
Desenne et al.

(10) Patent No.: US 9,095,528 B2
(45) Date of Patent: *Aug. 4, 2015

(54) COSMETIC COMPOSITION COMPRISING AT LEAST TWO VOLATILE LINEAR ALKANES AND AT LEAST ONE NONPROTEIN CATIONIC POLYMER

(75) Inventors: Patricia Desenne, Pringy (FR); Claire Bourdin, Levallois Perret (FR)

(73) Assignee: L'OREAL, Paris (FR)

( * ) Notice: Subject to any disclaimer, the term of this patent is extended or adjusted under 35 U.S.C. 154(b) by 474 days.

This patent is subject to a terminal disclaimer.

(21) Appl. No.: 12/977,227

(22) Filed: Dec. 23, 2010

(65) Prior Publication Data

US 2012/0009138 A1  Jan. 12, 2012

Related U.S. Application Data

(60) Provisional application No. 61/296,494, filed on Jan. 20, 2010.

(30) Foreign Application Priority Data

Dec. 23, 2009 (FR) .................................... 09 59482

(51) Int. Cl.

| A61Q 17/00 | (2006.01) |
|---|---|
| A61K 8/81 | (2006.01) |
| A61K 8/73 | (2006.01) |
| A61Q 5/00 | (2006.01) |
| A61K 8/89 | (2006.01) |
| A61K 8/64 | (2006.01) |
| A61K 8/31 | (2006.01) |
| A61Q 5/12 | (2006.01) |

(52) U.S. Cl.
CPC ................. *A61K 8/8182* (2013.01); *A61K 8/31* (2013.01); *A61K 8/8152* (2013.01); *A61Q 5/12* (2013.01); *A61K 2800/5426* (2013.01)

(58) Field of Classification Search
CPC ............ A61K 2039/505; A61K 45/06; A61K 47/48384; A61K 31/4168; A61K 31/4178; A61K 47/48561; A61K 47/48569; A61K 38/00; A61K 39/3955; A61K 47/48415; A61K 2039/507; A61K 31/519; A61K 31/5377

See application file for complete search history.

(56) References Cited

U.S. PATENT DOCUMENTS

| 3,874,870 | A | | 4/1975 | Green et al. |
|---|---|---|---|---|
| 4,387,090 | A | * | 6/1983 | Bolich, Jr. .................. 424/70.12 |
| 4,782,095 | A | * | 11/1988 | Gum ............................. 514/772 |
| 5,753,216 | A | * | 5/1998 | Leitch et al. ................ 424/70.12 |
| 5,811,383 | A | * | 9/1998 | Klier et al. .................... 510/417 |
| 2008/0269352 | A1 | * | 10/2008 | Falkowski et al. ............ 514/762 |

FOREIGN PATENT DOCUMENTS

| EP | 2 113 240 | 11/2009 |
|---|---|---|
| EP | 2 116 221 | 11/2009 |
| WO | WO 2010/026140 | 3/2010 |

OTHER PUBLICATIONS

Ciba Specialty Chemicals: Product Overview: Personal Care, Salcare (TM) SC 95. Published Dec. 2002.*
"78 Exxon Norpar 13", National Center for Forensic Science, http://ilrc.ucf.edu/sample_detail.php?sample_id=78, accessed online May 27, 2013.*
French Search Report issued Sep. 21, 2010, in FR 0959482, filed Dec. 23, 2009.
U.S. Appl. No. 12/977,183, filed Dec. 23, 2010, Desenne, et al.
U.S. Appl. No. 12/969,980, filed Dec. 16, 2010, Desenne, et al.
U.S. Appl. No. 12/975,705, filed Dec. 22, 2010, Desenne, et al.
U.S. Appl. No. 12/970,988, filed Dec. 17, 2010, Desenne, et al.
U.S. Appl. No. 12/977,257, filed Dec. 23, 2010, Desenne, et al.
U.S. Appl. No. 12/977,204, filed Dec. 23, 2010, Desenne, et al.
U.S. Appl. No. 12/975,632, filed Dec. 22, 2010, Desenne, et al.

* cited by examiner

*Primary Examiner* — Audrea Buckley
(74) *Attorney, Agent, or Firm* — Oblon, McClelland, Maier & Neustadt, L.L.P.

(57) ABSTRACT

Composition containing, in a cosmetically acceptable medium, two or more volatile linear alkanes, and one or more nonprotein cationic polymers, with a volatile linear alkanes/polymer(s) ratio by weight of greater than or equal to 1.2. Use in the treatment of keratinous substances, preferably keratinous fibres, such as the hair.

18 Claims, No Drawings

COSMETIC COMPOSITION COMPRISING AT LEAST TWO VOLATILE LINEAR ALKANES AND AT LEAST ONE NONPROTEIN CATIONIC POLYMER

REFERENCE TO PRIOR APPLICATIONS

This application claims priority to U.S. provisional application Ser. No. 61/296,494, filed Jan. 20, 2010; and to French patent application 09 59482, filed Dec. 23, 2009, both incorporated herein by reference.

The present invention relates to a cosmetic composition comprising at least two volatile linear alkanes and at least one nonprotein cationic polymer, to its use in the cosmetic treatment of keratinous substances, preferably keratinous fibres, such as the hair, and to a method for the cosmetic treatment of keratinous substances employing the said composition.

In the field of hair treatment, the use of volatile solvents is known in rinse-out or leave-in hair care products. They are generally used for different reasons. They make it possible in particular to modify the sensory rendering of a hair product by conferring on it a light texture which is nonsticky in the hand. They can also confer on it a slipping nature which facilitates the distribution of the product over the hair and in particular over dry hair.

In aqueous emulsions of oil-in-water type, which can be provided in the form of more or less gelled creams, the addition of volatile solvents can also make it possible to dissolve silicone gums which, due to their intrinsic viscosity, would be difficult to introduce into the compositions.

These volatile solvents, which are generally liquid fatty esters, hydrocarbon oils of isododecane or isohexadecane type and/or silicone oils, can in particular result in problems of a greasy feel, of lack of sheen and of stiffened and hard hair.

There thus remains a need to replace these volatile solvents in order to avoid the abovementioned disadvantages.

The Applicant has now discovered, unexpectedly and surprisingly, that the combination of at least two volatile linear alkanes and of at least one nonprotein cationic polymer makes it possible to avoid the abovementioned disadvantages and to improve the cosmetic properties, such as the smoothing, the sheen, the transformation of the fibre on rinsing, the disentangling, the lightness, the suppleness, the softness, the volumizing giving effect and the definition of the curls on curly hair.

The term "transformation of the fibre on rinsing" is understood to mean a fibre immediately rendered supple, soft and smooth at the moment when the rinse-out care product is rinsed out.

A "volumizing effect" is obtained when an effect of weight of the hair and a feeling of overall density of the hair is felt in the hand.

In particular, the application to wet hair makes it possible to obtain wet hair which is smoother and shinier. In addition, dry hair is smooth and tidy without heaviness.

Thus, a subject-matter of the invention is a cosmetic composition comprising, in a cosmetically acceptable medium, two or more than two volatile linear alkanes and one, two or more than two nonprotein cationic polymers in a volatile linear alkanes/nonprotein cationic polymer(s) ratio by weight of greater than or equal to 1.2.

A further subject-matter of the invention is the use of the said composition in the cosmetic treatment of keratinous substances, preferably keratinous fibres, such as the hair.

Another subject-matter of the invention is a method for the cosmetic treatment of keratinous substances, preferably keratinous fibres, such as the hair, employing the said composition.

The cosmetic composition according to the invention comprises, in a cosmetically acceptable medium:
two or more volatile linear alkanes and
one or more nonprotein cationic polymers,
in a volatile linear alkanes/nonprotein cationic polymer(s) ratio by weight of greater than or equal to 1.2.

According to one embodiment, the cosmetic composition comprises, in a cosmetically acceptable medium:
two or more linear C7-15 alkanes, preferably C8-14 alkanes, and
one or more nonprotein cationic polymers
in a volatile linear alkanes/nonprotein cationic polymer(s) ratio by weight of greater than or equal to 1.2.

The said ratio preferably ranges from 1.2 to 50, better still from 2 to 30 and even better still from 3 to 20.

The term "two or more volatile linear alkanes" is understood to mean, without distinction, "two or more volatile linear alkane oils".

A volatile linear alkane suitable for the invention is liquid at ambient temperature (approximately 25° C.) and at atmospheric pressure (101 325 Pa or 760 mmHg).

The term "volatile linear alkane" suitable for the invention is understood to mean a linear alkane which is capable of evaporating on contact with the skin in less than one hour at ambient temperature (25° C.) and at atmospheric pressure (101 325 Pa), which is liquid at ambient temperature and which has in particular a rate of evaporation ranging from 0.01 to 15 mg/cm$^2$/min at ambient temperature (25° C.) and at atmospheric pressure (101 325 Pa).

Preferably, the volatile linear alkanes suitable for the invention exhibit a rate of evaporation ranging from 0.01 to 3.5 mg/cm$^2$/min, better still from 0.01 to 1.5 mg/cm2/min, at ambient temperature (25° C.) and at atmospheric pressure (101 325 Pa).

More preferably, the volatile linear alkanes suitable for the invention exhibit a rate of evaporation ranging from 0.01 to 0.8 mg/cm$^2$/min, preferably from 0.01 to 0.3 mg/cm2/min and more preferably still from 0.01 to 0.12 mg/cm2/min, at ambient temperature (25° C.) and at atmospheric pressure (101 325 Pa).

The rate of evaporation of a volatile alkane in accordance with the invention (and more generally of a volatile solvent) can be evaluated in particular by means of the protocol described in WO 06/013413 and more particularly by means of the protocol described below.

15 g of volatile hydrocarbon solvent are introduced into a crystallizing dish (diameter: 7 cm) placed on a balance located in a chamber with a capacity of approximately 0.3 m3 regulated with regard to temperature (25° C.) and hygrometry (relative humidity 50%).

The volatile hydrocarbon solvent is allowed to freely evaporate, without being stirred, ventilation being provided by a fan (Papst-Motoren, reference 8550 N, rotating at 2700 revolutions/minute) arranged in the vertical position above the crystallizing dish containing the volatile hydrocarbon solvent, the blades being directed towards the crystallizing dish, at a distance of 20 cm with respect to the bottom of the crystallizing dish.

The weight of volatile hydrocarbon solvent remaining in the crystallizing dish is measured at regular time intervals.

The evaporation profile of the solvent is then obtained by plotting the curve of the amount of product evaporated (in mg/cm$^2$) as a function of the time (in min).

The rate of evaporation, which corresponds to the tangent at the origin of the curve obtained, is then calculated. The rates of evaporation are expressed in mg of volatile solvent evaporated per unit of surface area ($cm^2$) and per unit of time (minute).

According to a preferred embodiment, the volatile linear alkanes suitable for the invention have a nonzero vapour pressure (also known as saturated vapour pressure) at ambient temperature, in particular a vapour pressure ranging from 0.3 Pa to 6000 Pa.

Preferably, the volatile linear alkanes suitable for the invention have a vapour pressure ranging from 0.3 to 2000 Pa, better still from 0.3 to 1000 Pa, at ambient temperature (25° C.).

More preferably, the volatile linear alkanes suitable for the invention have a vapour pressure ranging from 0.4 to 600 Pa, preferably from 1 to 200 Pa and more preferably still from 3 to 60 Pa, at ambient temperature (25° C.).

According to one embodiment, a volatile linear alkane suitable for the invention can exhibit a flash point within the range varying from 30 to 120° C. and more particularly from 40 to 100° C. The flash point is in particular measured according to standard ISO 3679.

According to one embodiment, the volatile linear alkanes suitable in the invention can comprise from 7 to 15 carbon atoms, preferably from 8 to 14 carbon atoms and better still from 9 to 14 carbon atoms.

More preferably, the volatile linear alkanes suitable in the invention comprise from 10 to 14 carbon atoms and more preferably still from 11 to 14 carbon atoms.

A volatile linear alkane suitable for the invention can advantageously be of vegetable origin.

Preferably, the mixture of volatile linear alkanes present in the composition according to the invention comprises at least a 14C isotope of carbon (carbon-14). In particular, the 14C isotope can be present in a ratio by number of isotopes (or 14C/12C ratio) of greater than or equal to $1 \times 10^{-16}$, preferably of greater than or equal to $1 \times 10^{-15}$, more preferably of greater than or equal to $7.5 \times 10^{-14}$ and better still of greater than or equal to $1.5 \times 10^{13}$. Preferably, the 14C/12C ratio ranges from $6 \times 10^{-13}$ to $1.2 \times 10^{-12}$).

The amount of 14C isotopes in the mixture of volatile linear alkanes can be determined by methods known to a person skilled in the art, such as the Libby counting method, liquid scintillation spectrometry or accelerator mass spectrometry.

Such an alkane can be obtained, directly or in several stages, from a vegetable starting material, such as an oil, a butter, a wax, and the like.

Mention may be made, as examples of alkanes suitable for the invention, of the alkanes described in Patent Applications WO 2007/068371 and WO2008/155059. These alkanes are obtained from fatty alcohols, themselves obtained from coconut or palm oil.

Mention may be made, as examples of linear alkanes suitable for the invention, of n-heptane (C7), n-octane (C8), n-nonane (C9), n-decane (C10), n-undecane (C11), n-dodecane (C12), n-tridecane (C13), n-tetradecane (C14) and n-pentadecane (C15). According to a specific embodiment, the volatile linear alkanes are chosen from n-nonane, n-undecane, n-dodecane, n-tridecane and n-tetradecane.

According to a preferred embodiment, mention may be made of the mixtures of n-undecane (C11) and of n-tridecane (C13) obtained in Examples 1 and 2 of Application WO2008/155059.

Mention may also be made of the n-dodecane (C12) and the n-tetradecane (C14) sold by Sasol under the references Parafol 12-97 and Parafol 14-97 respectively, and their mixtures.

One embodiment consists in using a mixture of at least two distinct volatile linear alkanes differing from one another by a carbon number n of at least 1, in particular differing from one another by a carbon number of 1 or 2.

According to one embodiment, use is made of a mixture of at least two distinct volatile linear alkanes comprising from 10 to 14 carbon atoms and differing from one another by a carbon number of at least 1. Mention may be made, as examples, in particular of the C10/C11, C11/C12 or C12/C13 mixtures of volatile linear alkanes.

According to another embodiment, use is made of a mixture of at least two distinct volatile linear alkanes comprising from 10 to 14 carbon atoms and differing from one another by a carbon number of at least 2. Mention may be made, as examples, in particular of the C10/C12 or C12/C14 mixtures of volatile linear alkanes, for an even carbon number n, and the C11/C13 mixture, for an uneven carbon number n.

According to a preferred embodiment, use is made of a mixture of at least two distinct volatile linear alkanes comprising from 10 to 14 carbon atoms which differ from one another by a carbon number of at least 2 and in particular of a C11/C13 mixture of volatile linear alkanes or a C12/C14 mixture of volatile linear alkanes.

Other mixtures combining more than two volatile linear alkanes according to the invention, such as, for example, a mixture of at least three distinct volatile linear alkanes comprising from 7 to 15 carbon atoms which differ from one another by a carbon number of at least 1, can be used in the invention.

In the case of the mixtures of two volatile linear alkanes, the said two volatile linear alkanes preferably represent more than 95% by weight and better still more than 99% by weight of the mixture.

According to a specific form of the invention, in a mixture of volatile linear alkanes, the volatile linear alkane having the smallest carbon number is predominant in the mixture.

According to another form of the invention, use is made of a mixture of volatile linear alkanes in which the volatile linear alkane having the greatest carbon number is predominant in the mixture.

Mention may in particular be made, as examples of mixtures suitable for the invention, of the following mixtures:
  from 50 to 90% by weight, preferably from 55 to 80% by weight, more preferably from 60 to 75% by weight, of volatile linear Cn alkane with n ranging from 7 to 15,
  from 10 to 50% by weight, preferably from 20 to 45% by weight, preferably from 24 to 40% by weight, of volatile linear Cn+x alkane with x greater than or equal to 1, preferably x=1 or x=2, with n+x between 8 and 14,
  with respect to the total weight of the alkanes in the said mixture.

In particular, the said mixture of volatile linear alkanes can additionally comprise:
  less than 2% by weight, preferably less than 1% by weight, of branched hydrocarbons,
  and/or less than 2% by weight, preferably less than 1% by weight, of aromatic hydrocarbons,
  and/or less than 2% by weight, preferably less than 1% by weight and preferentially less than 0.1% by weight of unsaturated hydrocarbons,
  the said percentages being expressed with respect to the total weight of the mixture.

More particularly, the volatile linear alkanes suitable in the invention can be employed in the form of an n-undecane/n-tridecane mixture.

In particular, use will be made of a mixture of volatile linear alkanes comprising:

from 55 to 80% by weight, preferably from 60 to 75% by weight, of volatile linear C11 alkane (n-undecane) and from 20 to 45% by weight, preferably from 24 to 40% by weight, of volatile linear C13 alkane (n-tridecane), with respect to the total weight of the alkanes in the said mixture.

According to a specific embodiment, the mixture of alkanes is an n-undecane/n-tridecane mixture. In particular, such a mixture can be obtained according to Example 1 or Example 2 of Application WO 2008/155059.

According to another specific embodiment, use is made of the n-dodecane sold under the reference Parafol 12-97 by Sasol.

According to another specific embodiment, use is made of the n-tetradecane sold under the reference Parafol 14-97 by Sasol.

According to yet another embodiment, use is made of a mixture of n-dodecane and n-tetradecane.

The composition of the invention can comprise from 0.5 to 90% by weight, in particular from 1 to 50% by weight, more particularly from 3 to 40% by weight and better still from 3 to 30% by weight of volatile linear alkanes, with respect to the total weight of the composition.

The term "cationic polymer" is understood to mean any polymer comprising cationic groups and/or groups which can be ionized to give cationic groups.

The cationic polymers which can be used in accordance with the present invention can be chosen from all those already known per se as improving the cosmetic properties of hair treated with detergent compositions, namely, in particular, those described in Patent Application EP-A-0 337 354 and in French Patent Applications FR-A-2 270 846, 2 383 660, 2 598 611, 2 470 596 and 2 519 863.

The preferred cationic polymers are chosen from those which comprise units comprising primary, secondary, tertiary and/or quaternary amine groups which can either form part of the main polymer chain or can be carried by a side substituent directly connected to the latter.

The cationic polymers used have a weight-average molecular weight of greater than 105, preferably greater than 106 and better still of between 106 and 108. The cationic polymers are preferably non-silicone polymers.

The cationic polymers used in the present invention are nonprotein polymers, that is to say that they do not comprise any protein block or unit based on amino acid or on peptide. Mention may more particularly be made, as nonprotein cationic polymer, of polymers of the polyamine, polyaminoamide and polyquaternary ammonium type. These are known products.

The polymers of the polyamine, polyaminoamide or polyquaternary ammonium type which can be used in the composition of the present invention are those described in French Patents Nos. 2 505 348 and 2 542 997. Mention may be made, among these polymers, of:

(1) Homopolymers or copolymers derived from acrylic esters, methacrylic esters, acrylamides or methacrylamides and comprising at least one of the units of following formulae:

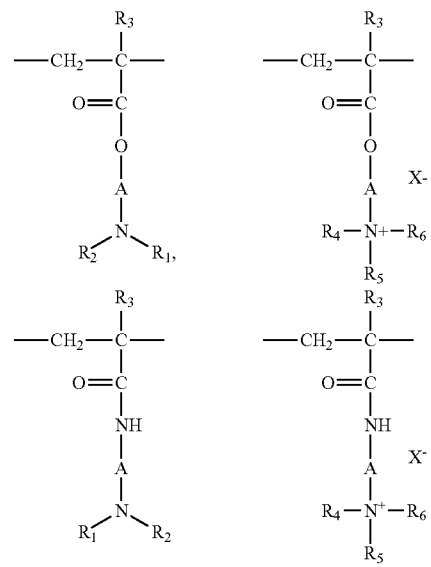

in which:

R1 and R2, which are identical or different, represent a hydrogen atom or an alkyl group having from 1 to 6 carbon atoms, and preferably a methyl or ethyl group;

R3, which are identical or different, denote a hydrogen atom or a CH3 group;

the symbols A, which are identical or different, represent a linear or branched alkyl group comprising from 1 to 6 carbon atoms, preferably 2 or 3 carbon atoms, or a hydroxyalkyl group comprising from 1 to 4 carbon atoms;

R4, R5 and R6, which are identical or different, represent an alkyl group having from 1 to 18 carbon atoms or a benzyl group, and preferably an alkyl group having from 1 to 6 carbon atoms;

X— denotes an anion derived from an inorganic or organic acid, such as a methyl sulphate anion or a halide, such as chloride or bromide.

The copolymers of the family (1) can additionally comprise one or more units deriving from comonomers which can be chosen from the family of the acrylamides, methacrylamides, diacetone acrylamides, acrylamides and methacrylamides substituted on the nitrogen atom by lower (C1-C4) alkyl groups, groups derived from acrylic or methacrylic acids or from their esters, from vinyllactams, such as vinylpyrrolidone or vinylcaprolactam, or from vinyl esters.

Thus, mention may be made, among these copolymers of the family (1), of:

copolymers of acrylamide and of dimethylaminoethyl methacrylate which is quaternized with dimethyl sulphate or with a methyl halide, copolymers of acrylamide and of methacryloyloxyethyltrimethylammonium chloride, described, for example, in Patent Application EP-A-080 976, the copolymer of acrylamide and of methacryloyloxyethyltrimethylammonium methyl sulphate, vinylpyrrolidone/dialkylaminoalkyl acrylate or methacrylate copolymers, which may or may not be quaternized. These polymers are described in detail in French Patents 2 077 143 and 2 393 573. Such a polymer is sold, for example, under the trade name Gafquat® 755 by ISP, dimethylaminoethyl methacrylate/vinylcaprolactam/vinylpyrrolidone terpolymers, vinylpyrrolidone/methacrylamidopropyldimethylamine copolymers, vinylpyrrolidone/quaternized dimethylaminopropyl-methacrylamide copolymers, and crosslinked polymers of methacryloyloxy(C1-C4)alkyltri (C1-C4)alkyl-ammonium salts, such as the polymers obtained by homopolymerization of dimethylaminoethyl methacrylate quaternized by methyl chloride or by copolymerization of acrylamide with dimethylaminoethyl methacrylate quaternized by methyl chloride, the homopolymerization or the copolymerization being followed by a crosslinking by a compound possessing olefinic unsaturation, in particular methylenebisacrylamide.

Mention may be made, as crosslinked polymers of methacryloyloxy(C1-C4)alkyltri(C1-C4)alkylammonium salts, of those sold under the names of Salcare® SC 92, Salcare® SC 95 and Salcare® SC 96 by Ciba.

(2) The cellulose ether derivatives comprising quaternary ammonium groups described in French Patent 1 492 597 and in particular the polymers sold under the "Ucare Polymer JR" (JR 400 LT, JR 125, JR 30M) or "Ucare Polymer LR" (LR 400, LR 30M) names by Amerchol. These polymers are also defined in the CTFA dictionary as quaternary ammoniums of hydroxyethylcellulose having reacted with an epoxide substituted by a trimethylammonium group.

(3) Cationic cellulose derivatives, such as copolymers of cellulose or cellulose derivatives which are grafted with a water-soluble quaternary ammonium monomer, and which are described in particular in U.S. Pat. No. 4,131,576, such as hydroxyalkylcelluloses, for example hydroxymethyl-, hydroxyethyl- or hydroxypropylcelluloses, grafted in particular with a methacryloylethyltrimethylammonium, methacrylamidopropyltrimethylammonium or dimethyldiallylammonium salt.

The commercially available products corresponding to this definition are more particularly the products sold under the names "Celquat® L 200" and "Celquat® H 100" by National Starch.

(4) The cationic polysaccharides described in U.S. Pat. Nos. 3,589,578 and 4,031,307, such as guar gums comprising trialkylammonium cationic groups. Use is made, for example, of guar gums modified by a 2,3-epoxypropyltrimethylammonium salt, for example the chloride.

Such products are sold in particular under the trade names of Jaguar® C 13 S, Jaguar® C15, Jaguar® C 17 or Jaguar® C162 by Rhodia.

(5) Polymers composed of piperazinyl units and of straight- or branched-chain divalent alkylene or hydroxyalkylene groups, optionally interrupted by oxygen, sulphur or nitrogen atoms or by aromatic or heterocyclic rings, as well as the oxidation and/or quaternization products of these polymers. Such polymers are described in particular in French Patents 2 162 025 and 2 280 361.

(6) Water-soluble polyaminoamides prepared in particular by polycondensation of an acidic compound with a polyamine; these polyaminoamides can be crosslinked by an epihalohydrin, a diepoxide, a dianhydride, an unsaturated dianhydride, a bisunsaturated derivative, a bishalohydrin, a bisazetidinium, a bishaloacyldiamine or an alkyl bishalide or alternatively by an oligomer resulting from the reaction of a bifunctional compound reactive with respect to a bishalohydrin, a bisazetidinium, a bishaloacyldiamine, an alkyl bishalide, an epihalohydrin, a diepoxide or a bisunsaturated derivative; the crosslinking agent being used in proportions ranging from 0.025 to 0.35 mol per amine group of the polyaminoamide; these polyaminoamides can be alkylated or, if they comprise one or more tertiary amine functional groups, quaternized. Such polymers are described in particular in French Patents 2 252 840 and 2 368 508.

(7) Polyaminoamide derivatives resulting from the condensation of polyalkylenepolyamines with polycarboxylic acids, followed by an alkylation by bifunctional agents. Mention may be made, for example, of adipic acid/dialkylaminohydroxyalkyldialkylenetriamine polymers in which the alkyl group comprises from 1 to 4 carbon atoms and preferably denotes a methyl, ethyl or propyl group and the alkylene group comprises from 1 to 4 carbon atoms and preferably denotes the ethylene group. Such polymers are described in particular in French Patent 1 583 363.

Mention may more particularly be made, among these derivatives, of the adipic acid/dimethylaminohydroxypropyldiethylenetriamine polymers.

(8) Polymers obtained by reaction of a polyalkylenepolyamine comprising two primary amine groups and at least one secondary amine group with a dicarboxylic acid chosen from diglycolic acid and saturated aliphatic dicarboxylic acids having from 3 to 8 carbon atoms; the molar ratio of polyalkylenepolyamine to dicarboxylic acid being between 0.8:1 and 1.4:1; the polyaminoamide resulting therefrom being brought to react with epichlorohydrin in a molar ratio of epichlorohydrin in relation to the secondary amine group of the polyaminoamide of between 0.5:1 and 1.8:1. Such polymers are described in particular in U.S. Pat. Nos. 3,227,615 and 2,961,347.

(9) Cyclopolymers of alkyldiallylamine or of dialkyldiallylammonium, such as the homopolymers or copolymers comprising, as main constituent of the chain, units corresponding to the formulae (Ia) or (Ib):

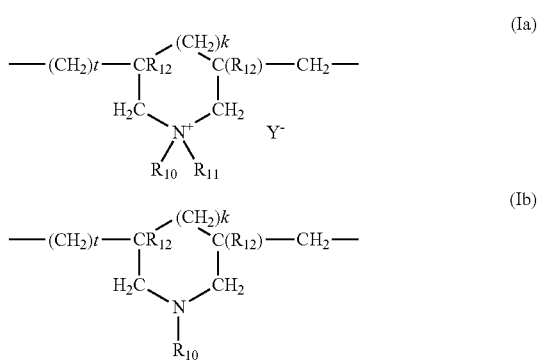

in which k and t are equal to 0 or 1, the sum k+t being equal to 1; R12 denotes a hydrogen atom or a methyl group; R10 and R11, independently of one another, denote an alkyl group having from 1 to 6 carbon atoms, a hydroxyalkyl group in which the alkyl group preferably has from 1 to 5 carbon atoms or a lower (C1-C4) amidoalkyl group or else R10 and R11 can denote, jointly with the nitrogen atom to which they are attached, heterocyclic groups, such as piperidinyl or morpholinyl; Y— is an anion, such as bromide, chloride, acetate, borate, citrate, tartrate, bisulphate, bisulphite, sulphate or phosphate. These polymers are described in particular in French Patent 2 080 759 and in its Certificate of Addition 2 190 406.

R10 and R11, independently of one another, preferably denote an alkyl group having from 1 to 4 carbon atoms.

Mention may more particularly be made, among the polymers defined above, of the homopolymer of dimethyldiallylammonium chloride sold under the name "Merquat® 100"

by Nalco Company (and its homologues of low weight-average molecular weights) and of the copolymers of diallyldimethylammonium chloride and of acrylamide sold under the name "Merquat® 550" or "Merquat® 7SPR".

(10) Diquaternary ammonium polymers comprising repeat units corresponding to the formula (II):

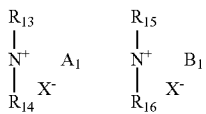

in which:

R13, R14, R15 and R16, which are identical or different, represent aliphatic, alicyclic or arylaliphatic groups comprising from 1 to 20 carbon atoms or lower aliphatic hydroxyalkyl groups or else R13, R14, R15 and R16, together or separately, constitute, with the nitrogen atoms to which they are attached, heterocycles optionally comprising a second heteroatom other than nitrogen or else R13, R14, R15 and R16 represent a linear or branched C1-C6 alkyl group substituted by a nitrile, ester, acyl, amide or —CO—O—R17-E or —CO—NH—R17-E group, where R17 is an alkylene group and F a quaternary ammonium group;

A1 and B1 represent polymethylene groups comprising from 2 to 20 carbon atoms which can be linear or branched and saturated or unsaturated, and which can comprise, bonded to or inserted into the main chain, one or more aromatic rings or one or more oxygen or sulphur atoms or sulphoxide, sulphone, disulphide, amino, alkylamino, hydroxyl, quaternary ammonium, ureido, amide or ester groups, and X— denotes an anion derived from an inorganic or organic acid;

A1, R13 and R15 can form, with the two nitrogen atoms to which they are attached, a piperazine ring; in addition, if A1 denotes a linear or branched, saturated or unsaturated, alkylene or hydroxyalkylene group, B1 can also denote a group:

—(CH2)n-CO-E'-OC—(CH2)n- in which E' denotes:

a) a glycol residue of formula —O—Z—O—, where Z denotes a linear or branched hydrocarbon group or a group corresponding to one of the following formulae:

—(CH2-CH2-O)x-CH2-CH2-

—[CH2-CH(CH3)-O]y-CH2-CH(CH3)- where x and y denote an integer from 1 to 4, representing a defined and unique degree of polymerization, or any number from 1 to 4, representing a mean degree of polymerization;

b) a bissecondary diamine residue, such as a piperazine derivative;

c) a bisprimary diamine residue of formula —NH—Y—NH—, where Y denotes a linear or branched hydrocarbon group or else the divalent group —CH2-CH2-S—S—CH2-CH2-;

d) a ureylene group of formula —NH—CO—NH—.

Preferably, X— is an anion, such as chloride or bromide.

Polymers of this type are described in particular in French Patents 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

Use may more particularly be made of the polymers which are composed of repeat units corresponding to the formula (III):

(VII)

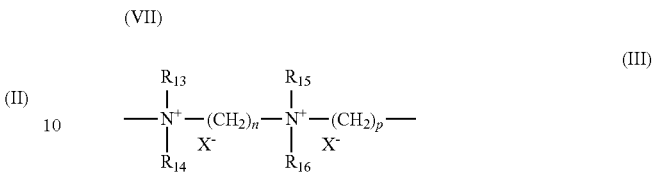

in which R13, R14, R15 and R16, which are identical or different, denote an alkyl or hydroxyalkyl group having from 1 to 4 carbon atoms approximately, n and p are integers varying from 2 to 20 approximately and X— is an anion derived from an inorganic or organic acid.

(11) Polyquaternary ammonium polymers composed of units of formula (IV):

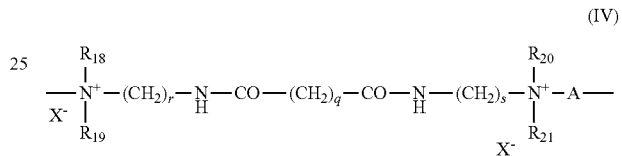

in which:

R18, R19, R20 and R21, which are identical or different, represent a hydrogen atom or a methyl, ethyl, propyl, β-hydroxyethyl, β-hydroxypropyl or —CH2CH2(OCH2CH2)pOH group, where p is equal to 0 or to an integer between 1 and 6, with the proviso that R18, R19, R20 and R21 do not simultaneously represent a hydrogen atom, r and s, which are identical or different, are integers between 1 and 6, q is equal to 0 or to an integer between 1 and 34, X— denotes an anion, such as a halide, A denotes a radical from a dihalide or preferably represents —CH2-CH2-O—CH2-CH2-.

Such compounds are described in particular in Patent Application EP-A-122 324.

(12) Quaternary polymers of vinylpyrrolidone and of vinylimidazole, such as, for example, the products sold under the names Luviquat® FC 905, FC 550 and FC 370 by BASF, and their mixtures.

Other cationic polymers which can be used in the context of the invention are polyalkyleneimines, in particular polyethyleneimines, polymers comprising vinylpyridine or vinylpyridinium units, condensates of polyamines and of epichlorohydrin, quaternary polyureylenes and chitin derivatives.

Preference is given, among all the cationic polymers capable of being used in the context of the present invention, to the use of those of the families (1), (2) (9) and (12) and more particularly of quaternized vinylpyrrolidone/dialkylaminoalkyl acrylate or methacrylate copolymers, such as that sold under the name Gafquat® 755 by ISP; cellulose ether derivatives comprising quaternary ammonium groups, such as the products sold under the name "Ucare Polymer JR 400 LT" by Amerchol; cationic cyclopolymers, in particular dimethyldiallylammonium chloride homopolymers or copolymers, sold under the names Merquat® 100, Merquat® 550, Merquat® S and Merquat® 7SPR by Nalco Company; quaternary polymers of vinylpyrrolidone and of vinylimidazole, such as, for example, the products sold under the names Luviquat® FC 905, FC 550 and FC 370 by BASF; crosslinked polymers of methacryloyloxy(C1-C4)alkyltri (C1-C4)alkylammonium salts, such as those sold under the names of Salcare® SC 92, Salcare® SC 95 and Salcare® SC 96 by Ciba; and their mixtures.

The nonprotein cationic polymers are preferably present in an amount ranging from 0.05 to 10% by weight, better still from 0.1 to 5% by weight and more preferably still from 0.2 to 2% by weight, with respect to the total weight of the composition.

The cosmetically acceptable medium is preferably composed of water or of a mixture of water and of at least one cosmetically acceptable solvent chosen from lower C1-C4 alcohols, such as ethanol, isopropanol, tert-butanol or n-butanol; polyols, such as glycerol, propylene glycol and polyethylene glycols; and their mixtures.

According to an embodiment, the composition according to the invention can additionally comprise at least one saturated or unsaturated and linear or branched fatty alcohol comprising from 8 to 32 carbon atoms, better still from 10 to 22 carbon atoms. Mention may in particular be made, as examples of fatty alcohols which can be used in the present invention, of lauryl alcohol, myristyl alcohol, cetyl alcohol, stearyl alcohol, cetearyl alcohol, oleyl alcohol, behenyl alcohol, hexyldecanol, 2-octyldodecanol, and their mixtures.

When the alcohol or the fatty alcohol(s) is/are present, the composition according to the invention can comprise from 0.1 to 20% by weight thereof, in particular from 0.2 to 15% by weight thereof and more particularly from 0.5 to 10% by weight thereof, with respect to the total weight of the composition.

Preferably, the composition according to the invention can further comprise at least one fatty ester and/or at least one silicone which is preferably non-volatile.

In one embodiment, the composition according to the invention can additionally comprise at least one fatty ester of a C2-30 mono- or polycarboxylic acid and of a C1-30, preferably C3-20, mono- or polyalcohol, the total number of carbon atoms in the ester varying from 10 to 50. In particular, the carboxylic acid and the alcohol of the fatty ester are linear.

Mention may in particular be made, as examples of fatty esters which can be used in the present invention, of 2-ethylhexyl caprate/caprylate (or octyl caprate/caprylate), ethyl laurate, butyl laurate, hexyl laurate, isohexyl laurate, isopropyl laurate, methyl myristate, ethyl myristate, butyl myristate, isobutyl myristate, isopropyl myristate, 2-octyldodecyl myristate, myristyl myristate, cetyl myristate, stearyl myristate, 2-ethylhexyl monococoate (or octyl monococoate), methyl palmitate, ethyl palmitate, isopropyl palmitate, isobutyl palmitate, 2-ethylhexyl palmitate (or octyl palmitate), myristyl palmitate, cetyl palmitate, stearyl palmitate, butyl stearate, isopropyl stearate, isobutyl stearate, isocetyl stearate, myristyl stearate, cetyl stearate, stearyl stearate, isostearyl isostearate, isopropyl isostearate, 2-ethylhexyl stearate (or octyl stearate), 2-ethylhexyl pelargonate (or octyl pelargonate), 2-ethylhexyl hydroxystearate (or octyl hydroxystearate), decyl oleate, diisopropyl adipate, di-2-ethylhexyl adipate (or dioctyl adipate), diisocetyl adipate, 2-ethylhexyl succinate (or octyl succinate), diisopropyl sebacate, 2-ethylhexyl malate (or octyl malate), pentaerythritol caprate/caprylate, pentaerythritol tetraisostearate, 2-ethylhexyl hexanoate (or octyl hexanoate), octyldodecyl octanoate, isodecyl neopentanoate, isostearyl neopentanoate, cetearyl isononanoate, isodecyl isononanoate, isononyl isononanoate, isotridecyl isononanoate, lauryl lactate, myristyl lactate, cetyl lactate, myristyl propionate, 2-ethylhexyl 2-ethylhexanoate (or octyl 2-ethylhexanoate), 2-ethylhexyl octanoate (or octyl octanoate), C12-15 fatty alcohol benzoates (Finsolv TN from Finetex), isopropyl lauroyl sarcosinate (Eldew SL 205 from Unipex), dicaprylyl carbonate (Cetiol CC from Cognis) and their mixtures.

Preferably, the fatty ester can be chosen from myristyl myristate, cetyl myristate, stearyl myristate, myristyl palmitate, cetyl palmitate, stearyl palmitate, myristyl stearate, cetyl stearate, stearyl stearate and their mixtures.

When the fatty ester or the fatty esters is or are present, the composition according to the invention can comprise from 0.1 to 20% by weight thereof, in particular from 0.5 to 15% by weight thereof and more particularly from 1 to 10% by weight thereof, with respect to the total weight of the composition.

The composition according to the invention can additionally comprise at least one other solid fatty substance, such as waxes, other than the fatty alcohols or the esters defined above.

The term "wax" is understood to mean, within the meaning of the present invention, a lipophilic compound which is solid at ambient temperature (25° C.), which exhibits a reversible solid/liquid change in state and which has a melting point of greater than or equal to 30° C. which can range up to 200° C. and in particular up to 120° C.

On bringing a wax to the liquid state (melting), it is possible to render it miscible with the oils and to form a macroscopically homogeneous mixture but, on bringing the temperature of the mixture to ambient temperature, recrystallization of the wax in the oils of the mixture is obtained.

A wax suitable for the invention can exhibit a melting point of greater than or equal to 45° C. and in particular of greater than or equal to 55° C.

Within the meaning of the invention, the melting point corresponds to the temperature of the most endothermic peak observed by thermal analysis (DSC) as described in Standard ISO 11357-3; 1999. The melting point of the wax can be measured using a differential scanning calorimeter (DSC), for example the calorimeter sold under the name "MDSC 2920" by TA Instruments.

In particular, a wax suitable for the invention can be chosen from waxes of animal, vegetable, mineral or synthetic origin and their mixtures.

Mention may in particular be made, by way of illustration of waxes suitable for the invention, of hydrocarbon waxes, such as beeswax, in particular of biological origin, lanolin wax, Chinese insect waxes, rice bran wax, carnauba wax, candelilla wax, ouricury wax, esparto wax, berry wax, shellac wax, Japan wax, sumac wax, montan wax, orange and lemon waxes, microcrystalline waxes, paraffin waxes, ozokerite, polyethylene waxes, the waxes obtained by the Fischer-Tropsch synthesis and waxy copolymers, and also their esters.

Mention may also be made of C20-C60 microcrystalline waxes such as Microwax HW.

Mention may also be made of the PM 500 polyethylene wax sold under the reference Permalen 50-L polyethylene.

Mention may also be made of waxes obtained by catalytic hydrogenation of animal or vegetable oils having linear or branched C8-C32 fatty chains.

Mention may in particular be made, among these, of isomerized jojoba oil, such as the trans isomerized partially hydrogenated jojoba oil manufactured or sold by Desert Whale under the commercial reference Iso-Jojoba-50®, hydrogenated sunflower oil, hydrogenated castor oil, hydrogenated coconut oil, hydrogenated lanolin oil and di(1,1,1-trimethylolpropane)tetrastearate, sold under the name of Hest 2T-4S® by Heterene.

Mention may also be made of fluorinated waxes.

Use may also be made of the waxes obtained by hydrogenation of castor oil esterified with cetyl alcohol which are sold under the names of Phytowax Castor 16L64® and 22L73® by Sophim. Such waxes are described in Application FR-A-2 792 190.

Use may be made, as wax, of a C20-C40 alkyl (hydroxystearyloxy)stearate (the alkyl group comprising from 20 to 40 carbon atoms), alone or as a mixture.

Such a wax is sold in particular under the names "Kester Wax K 82 P®", "Hydroxypolyester K 82 PR" and "Kester Wax K 80 PR" by Koster Keunen.

Mention may in particular be made, as microwaxes which can be used in a composition of the invention, of carnauba microwaxes, such as that sold under the name of MicroCare 350® by Micro Powders, synthetic wax microwaxes, such as that sold under the name of MicroEase 114S® by Micro Powders, microwaxes composed of a mixture of carnauba wax and of polyethylene wax, such as those sold under the names of MicroCare 300® and 310® by Micro Powders, microwaxes composed of a mixture of carnauba wax and of synthetic wax, such as that sold under the name MicroCare 325® by Micro Powders, polyethylene microwaxes, such as those sold under the names of Micropoly 200®, 220®, 220L® and 250S® by Micro Powders, and polytetrafluoroethylene microwaxes such as those sold under the names of Microslip 519® and 519 L® by Micro Powders.

According to an embodiment, a wax suitable for the invention can be chosen in particular from candelilla wax, carnauba wax, rice bran wax, beeswax, in particular certified biological beeswax, isomerized jojoba oil and their mixtures.

When it/they is/are present, the composition according to the invention can comprise from 0.1 to 20% by weight of wax(es), in particular from 0.2 to 10% by weight, more particularly from 0.5 to 5% by weight and better still from 0.5 to 3% by weight of wax(es), with respect to the total weight of the composition.

In one embodiment, the composition according to the invention can additionally comprise at least one silicone.

The silicones which may be used in accordance with the invention can be volatile or nonvolatile, and preferably non-volatile.

The silicones which may be used in accordance with the invention can be soluble or insoluble in the composition. They can in particular be polyorganosiloxanes which are insoluble in the composition of the invention and be provided in the form of oils, of waxes, of resins or of gums.

The insoluble silicones are in particular dispersed in the compositions in the form of particles generally having a number-average size of between 2 nanometres and 100 micrometres, preferably between 20 nanometres and 20 micrometres (measured with a particle sizer).

Organopolysiloxanes are defined in more detail in the work by Walter Noll, "Chemistry and Technology of Silicones", (1968) Academic Press. They can be volatile or nonvolatile, and preferably nonvolatile.

When they are volatile, the silicones are chosen more particularly from those having a boiling point of between 60° C. and 260° C. and more particularly still from:

(i) cyclic silicones comprising from 3 to 7 silicon atoms and preferably 4 or 5. They are, for example, octamethylcyclotetrasiloxane, sold in particular under the name of "Volatile Silicone 7207" by Union Carbide or "Silbione 70045 V 2" by Rhodia, decamethylcyclopentasiloxane, sold under the name of "Volatile Silicone 7158" by Union Carbide or "Silbione 70045 V 5" by Rhodia, and their mixtures.

Mention may also be made of cyclocopolymers of the dimethylsiloxane/methylalkylsiloxane type, such as "Silicone Volatile FZ 3109", sold by Union Carbide, with the chemical structure:

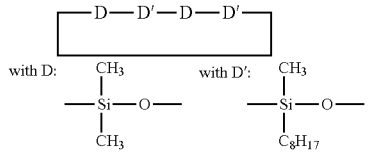

Mention may also be made of mixtures of cyclic silicones with silicon-derived organic compounds, such as the mixture of octamethylcyclotetrasiloxane and of tetratrimethylsilylpentaerythritol (50/50) and the mixture of octamethylcyclotetrasiloxane and of 1,1'-oxy(hexa-2,2,2',2',3,3'-trimethylsilyloxy)bisneopentane;

(ii) linear volatile silicones having from 2 to 9 silicon atoms and having a viscosity of less than or equal to $5 \times 10^{-6}$ m2/s at 25° C. They are, for example, decamethyltetrasiloxane, sold in particular under the name "SH 200" by Toray Silicone. Silicones coming within this category are also described in the article published in Cosmetics and Toiletries, Vol. 91, January 76, pp. 27-32, Todd & Byers, "Volatile Silicone Fluids for Cosmetics".

Mention may in particular be made, among nonvolatile silicones, of polyalkylsiloxanes, polyarylsiloxanes, polyalkylarylsiloxanes, silicone gums and resins, polyorganosiloxanes modified by organofunctional groups, polysiloxane (A)-polyoxyalkylene(B) linear block copolymers of (A-B)n type with n>3, grafted silicone polymers having a non-silicone organic backbone, composed of an organic main chain formed from organic monomers not comprising silicone, to which is grafted, inside the said chain and optionally at one at least of its ends, at least one polysiloxane macromonomer, grafted silicone polymers having a polysiloxane backbone grafted with non-silicone organic monomers, comprising a polysiloxane main chain to which is grafted, inside the said chain and optionally at one at least of its ends, at least one organic macromonomer not comprising silicone, and their mixtures.

Mention may in particular be made, as examples of polyalkylsiloxanes, of polydimethylsiloxanes possessing trimethylsilyl end groups having a viscosity of $5 \times 10^{-6}$ to 2.5 m2/s at 25° C. and preferably of $1 \times 10^{-5}$ to 1 m2/s. The viscosity of the silicones for example, measured at 25° C. according to Standard ASTM 445 Appendix C.

Mention may be made, among these polyalkylsiloxanes, without implied limitation, of the following commercial products:

Silbione oils of the 47 and 70 047 series or Mirasil oils sold by Rhône-Poulenc, such as, for example, the oil 70 047 V 500 000;
  oils of the Mirasil series sold by Rhône-Poulenc;
  oils of the 200 series from Dow Corning, such as, more particularly, DC200 with a viscosity of 60 000 cSt;
  Viscasil oils from General Electric and some oils of the SF series (SF 96, SF 18) from General Electric.

Mention may also be made of polydimethylsiloxanes possessing dimethylsilanol end groups (dimethiconol according to the CTFA name), such as oils of the 48 series from Rhône-Poulenc.

Mention may also be made, in this category of polyalkylsiloxanes, of the products sold under the names "Abil Wax 9800" and "Abil Wax 9801" by Goldschmidt, which are poly (C1-C20)alkylsiloxanes.

The polyalkylarylsiloxanes can in particular be chosen from linear and/or branched polydimethyl(methylphenyl)siloxanes or polydimethyldiphenylsiloxanes with a viscosity of 1×10-5 to 5×10-2 m2/s at 25° C.

Mention may be made, among these polyalkylarylsiloxanes, by way of example, of the products sold under the following names:

Silbione oils of the 70 641 series from Rhône-Poulenc;
oils of the Rhodorsil 70 633 and 763 series from Rhône-Poulenc;
the oil Dow Corning 556 Cosmetic Grade Fluid from Dow Corning;
silicones of the PK series from Bayer, such as the product PK20;
silicones of the PN and PH series from Bayer, such as the products PN1000 and PH1000;
some oils of the SF series from General Electric, such as SF 1023, SF 1154, SF 1250 and SF 1265.

Silicone gums which can be used in accordance with the invention are in particular polydiorganosiloxanes having high number-average molecular weights of between 200 000 and 1 000 000, used alone or as a mixture in a solvent. This solvent can be chosen from volatile silicones, polydimethylsiloxane (PDMS) oils, polyphenylmethylsiloxane (PPMS) oils, isoparaffins, polyisobutylenes, methylene chloride, pentane, dodecane, tridecanes or their mixtures.

Mention may more particularly be made of the following products:

polydimethylsiloxane gums,
polydimethylsiloxane/methylvinylsiloxane gums,
polydimethylsiloxane/diphenylsiloxane gums,
polydimethylsiloxane/phenylmethylsiloxane gums,
polydimethylsiloxane/diphenylsiloxane/methylvinylsiloxane gums.

Silicones which may be used in the composition according to the invention are mixtures, such as:

mixtures formed from a polydimethylsiloxane hydroxylated at the chain end (named dimethiconol according to the nomenclature of the CTFA dictionary) and from a cyclic polydimethylsiloxane (named cyclomethicone according to the nomenclature of the CTFA dictionary), such as the product Q2 1401 sold by Dow Corning;
mixtures formed from a polydimethylsiloxane gum with a cyclic silicone, such as the product SF 1214 Silicone Fluid from General Electric; this product is a gum SF 30, corresponding to a dimethicone, having a number-average molecular weight of 500 000, dissolved in the oil SF 1202 Silicone Fluid, corresponding to decamethylcyclopentasiloxane;
mixtures of two PDMSs with different viscosities and more particularly of a PDMS gum and of a PDMS oil, such as the product SF 1236 from General Electric. The product SF 1236 is the mixture of a gum SE 30 defined above, having a viscosity of 20 m2/s, and of an oil SF 96 with a viscosity of 5×10-6 m2/s. This product preferably comprises 15% of gum SE 20 and 85% of an oil SF 96.

The organopolysiloxane resins which can be used in accordance with the invention are crosslinked siloxane systems including the units: R2SiO2/2, R3SiO1/2, RSiO3/2 and SiO4/2, in which R represents a hydrocarbon group having from 1 to 16 carbon atoms or a phenyl group.

Among these products, those which are particularly preferred are those in which R denotes a lower C1-C4 alkyl radical, more particularly methyl, or a phenyl radical.

Mention may be made, among these resins, of the product sold under the name "Dow Corning 593" or those sold under the names "Silicone Fluid SS 4230" and "Silicone Fluid SS 4267" by General Electric and which are silicones with a dimethyl/trimethylsiloxane structure.

Mention may also be made of resins of the trimethylsiloxysilicate type, sold in particular under the names X22-4914, X21-5034 and X21-5037 by Shin-Etsu.

The organomodified silicones which can be used in accordance with the invention are silicones as defined above which comprise, in their structure, one or more organofunctional groups attached via a hydrocarbon group.

Mention may be made, among organomodified silicones, of the polyorganosiloxanes comprising:

polyethyleneoxy and/or polypropyleneoxy groups optionally comprising C6-C24 alkyl groups, such as the products known as dimethicone copolyol, sold by Dow Corning under the name DC 1248, or the Silwet® L 722, L 7500, L 77 and L 711 oils from Union Carbide, and (C12)alkyl methicone copolyol, sold by Dow Corning under the name Q2 5200;
substituted or unsubstituted amino groups, such as the products sold under the names GP 4 Silicone Fluid and GP 7100 by Genesee or the products sold under the names Q2 8220 and Dow Corning 929 or 939 by Dow Corning. The substituted amino groups are in particular amino (C1-C4 alkyl) groups;
quaternary ammonium groups, such as the products sold under the names Abilquat 3272 and Abilquat 3474 by Goldschmidt;
thiol groups, such as the products sold under the names "GP 72 A" and "GP 71" from Genesee;
alkoxylated groups, such as the product sold under the name "Silicone Copolymer F-755" by SWS Silicones and Abil Wax® 2428, 2434 and 2440 by Goldschmidt;
hydroxylated groups, such as the polyorganosiloxanes possessing a hydroxyalkyl functional group described in French Patent Application FR-A-85 16334;
acyloxyalkyl groups, such as, for example, the polyorganosiloxanes described in U.S. Pat. No. 4,957,732;
anionic groups of the carboxylic acid type, such as, for example, in the products described in Patent EP 186 507 from Chisso Corporation, or of the alkylcarboxyl type, such as those present in the product X-22-3701 E from Shin-Etsu; 2-hydroxyalkyl-sulphonate; 2-hydroxyalkyl thiosulphate, such as the products sold by Goldschmidt under the names "Abil® 5201" and "Abil® S255";
hydroxyacylamino groups, such as the polyorganosiloxanes described in Application EP 342 834. Mention may be made, for example, of the product Q2-8413 from Dow Corning.

The silicones which are particularly preferred in the invention are polydimethylsiloxanes possessing trimethylsilyl or dimethylsilanol end functional groups, polydimethylsiloxanes possessing amine functional groups, and their mixtures.

In a specific embodiment, the silicone is a polydimethylsiloxane possessing trimethylsilyl end functional groups, such as that sold under the trade name Belsil DM 300 000 by Wacker.

When at least one of the said silicones is present, it/they is/are preferably present in an amount ranging from 0.1 to 20% by weight, more particularly from 0.2 to 10% by weight, better still from 0.5 to 5% by weight and even better still from 0.5 to 4% by weight, with respect to the total weight of the composition.

The composition according to the invention can additionally comprise one or more conventional additives well known in the art, such as ionic or nonionic associative or nonassociative polymers, polyols, proteins, vitamins, reducing agents, plasticizers, softeners, antifoaming agents, moisturizing agents, pigments, clays, inorganic fillers, UV screening agents, inorganic colloids, peptizing agents, solubilizing agents, fragrances, preservatives, anionic, cationic, nonionic or amphoteric surfactants, pearlescent agents, propellants, inorganic or organic thickeners, antidandruff agents, grease-control agents, agents for combatting hair loss or for hair growth.

A person skilled in the art will take care to choose the optional additives and their amounts so that they do not harm the properties of the compositions of the present invention.

These additives are generally present in the composition according to the invention in an amount ranging from 0 to 20% by weight, with respect to the total weight of the composition.

The compositions according to the invention can be provided in the form of rinse-out or leave-in care compositions, these being provided in the form of a more or less thickened lotion, of a cream, of a gel or of an emulsion.

Another subject-matter of the invention is the use of the cosmetic composition as described above in the cosmetic treatment of keratinous substances, preferably keratinous fibres, such as the hair.

The invention also relates to a method for the cosmetic treatment of keratinous substances, preferably keratinous fibres, such as the hair, which consists in applying an effective amount of a cosmetic composition as described above to the said substances and in optionally rinsing out after an optional leave-in time.

When the composition according to the invention is applied in the form of a lotion or of a cream, it is optionally left standing on the hair for approximately ½ min to 5 minutes and then rinsing with water is optionally carried out.

The following examples are given by way of illustration of the present invention.

In the following examples, all the amounts are indicated as per cent by weight of product as is, with respect to the total weight of the composition, unless otherwise indicated.

EXAMPLES

Example 1

The following rinse-out care composition was prepared from the ingredients shown in the table below.

| | |
|---|---|
| Mixture predominantly composed of n-undecane and of n-tridecane according to Example 2 of WO 2008/155059 | 8.5% |
| Crosslinked ethyltrimethylammonium methacrylate chloride homopolymer, as an inverse emulsion comprising 50% of AM in a mineral oil, sold under the trade name Salcare SC 95 by Ciba | 1% |
| Cetearyl (C16/C18 50/50) alcohol, sold under the trade name Lanette O OR by Cognis | 8% |
| Myristyl/cetyl/stearyl myristate/palmitate/stearate mixture, sold under the trade name Crodamol MS-PA(MH) by Croda | 1.5% |
| Polydimethylsiloxane, sold under the trade name Belsil DM 300 000 by Wacker Chemie AG | 1.5% |
| Candellila wax | 2% |
| Polyethylene glycol distearate (150 mol of ethylene oxide), sold under the trade name Kessco PEG 6000 DS by Italmatch Chemicals Arese | 0.5% |
| Pregelatinized hydroxypropyl maize distarch phosphate, as an aqueous dispersion comprising 88% of AM (Structure Zea from Akzo Nobel) | 0.2% |
| PEG-150/stearyl alcohol/SMDI copolymer at 15% by weight in a maltodextrin/water matrix, sold under the trade name Aculyn 46 by Röhm & Haas | 3% |
| Preservative | q.s. |
| Fragrance | q.s. |
| Water q.s. for | 100% |

AM: Active Material

This rinse-out care composition was tested on heads and compared with an identical comparative composition comprising a volatile silicone solvent, a cyclopentasiloxane, in place of the mixture of undecane and of tridecane. These compositions were applied at ambient temperature to hair for one minute and subsequently rinsed out.

An improvement in the smoothing, in the softness and in the suppleness was observed with the composition according to the invention, in comparison with the comparative composition.

This improvement was also observed when the mixture of undecane and of tridecane was replaced with n-dodecane, n-tetradecane or the mixture of n-dodecane and of n-tetradecane in the composition, in comparison with the comparative composition comprising the cyclopentasiloxane.

Example 2

The following leave-in care composition was prepared from the ingredients shown in the table below.

| | |
|---|---|
| n-Dodecane/n-tetradecane mixture, sold under the trade name Vegelight 1214 by Biosynthis | 2% |
| Crosslinked ethyltrimethylammonium methacrylate chloride homopolymer, as a dispersion in a mixture of esters at 50%, sold under the trade name Salcare SC 96 by Ciba | 1% |
| Polydimethylsiloxane, sold under the trade name Belsil DM 300 000 by Wacker Chemie AG | 2% |
| PEG-150/stearyl alcohol/SMDI copolymer, at 15% by weight in a maltodextrin/water matrix, sold under the trade name Aculyn 46 by Röhm & Haas | 2.5% |
| Preservatives | q.s. |
| Fragrance | q.s. |
| Water q.s. for | 100% |

This composition was applied to the hair. After drying, excellent smoothing, softness and suppleness results were observed.

Example 3

The following leave-in care composition was prepared from the ingredients shown in the table below.

| | |
|---|---|
| Mixture predominantly composed of n-undecane/n-tridecane according to Example 2 of WO 2008/155059 | 3% |
| Vinylpyrrolidone/methylvinylimidazolium chloride (70/30) copolymer, as an aqueous solution comprising 40% of AM, sold under the trade name Luviquat FC 370 by BASF | 2.5% |
| Dimethyldiallylammonium chloride/acrylamide (30/70 in moles) copolymer, as a 9.5% by weight aqueous solution, sold under the trade name Merquat 7SPR by Nalco Company | 1% |
| Polydimethylsiloxane, sold under the trade name Belsil DM 300 000 by Wacker Chemie AG | 3% |
| 2-Amino-2-methyl-1-propanol | 0.55% |
| Phenyltrimethylsiloxytrisiloxane sold under the trade name Dow Corning 556 Cosmetic Grade Fluid by Dow Corning | 0.5% |
| Oxyethylenated hydrogenated castor oil (40 mol of ethylene oxide) | 0.5% |
| Acrylates/C10-C30 acrylate crosspolymer, sold under the trade name Pemulen TR-1 Polymer by Lubrizol | 0.6% |
| Hydroxyethylcellulose quaternized with 2,3-epoxypropyl-trimethylammonium chloride, sold under the trade name Ucare Polymer JR 400 LT by Amerchol | 0.4% |
| Preservatives | q.s. |
| Fragrance | q.s. |
| Water q.s. for | 100% |

AM: Active Material

This composition was applied to the hair. After drying, very good visual smoothing, an excellent feel and a very great ease of shaping were observed.

The visual smoothing and the ease of shaping are superior to those obtained with an identical composition in which the undecane/tridecane mixture is replaced with cyclopentasiloxane.

Example 4

The following leave-in care composition was prepared from the ingredients shown in the table below.

| | |
|---|---|
| Mixture predominantly composed of n-undecane/n-tridecane according to Example 2 of WO 2008/155059 | 1% |
| Vinylpyrrolidone/dimethylaminoethyl methacrylate copolymer quaternized with diethyl sulphate, as an aqueous solution comprising 20% of AM, sold under the trade name Gafquat 755 by ISP | 1% |
| Crosslinked ethyltrimethylammonium methacrylate chloride homopolymer, as a dispersion in a mixture of esters at 50%, sold under the trade name Salcare SC 96 by Ciba | 1% |
| Polydimethylsiloxane possessing aminoethyliminopropyl groups, possessing methoxy and/or hydroxy and α,ω-silanol functional groups, as a 60% cationic aqueous emulsion, sold under the trade name Dow Corning 2-8299 Cationic emulsion by Dow Corning | 1% |
| Oxyethylenated hydrogenated castor oil (40 mol of ethylene oxide) | 1.5% |
| Glycerol | 3% |
| Octane-1,2-diol | 0.5% |
| Preservatives | q.s. |
| Fragrance | q.s. |
| Water q.s. for | 100% |

AM: Active Material

This composition was applied to the hair. After drying, very good visual smoothing, an excellent feel and a very good ease of shaping were observed.

The visual smoothing and the ease of shaping are superior to those obtained with an identical composition in which the undecane/ tridecane mixture is replaced with cyclopentasiloxane.

The compositions given in the examples may be sprayable, for example via a pump-action spray.

The composition of Example 4 was packaged in a pump-action spray. It was then possible to easily distribute the sprayed composition over the hair.

The above written description of the invention provides a manner and process of making and using it such that any person skilled in this art is enabled to make and use the same, this enablement being provided in particular for the subject matter of the appended claims, which make up a part of the original description.

As used herein, the words "a" and "an" and the like carry the meaning of "one or more."

The phrases "selected from the group consisting of," "chosen from," and the like include mixtures of the specified materials. Terms such as "contain(s)" and the like are open terms meaning 'including at least' unless otherwise specifically noted.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may he applied to other embodiments and applications without departing from the spirit and scope of the invention. Thus, this invention is not intended to be limited to the embodiments shown, but is to be accorded the widest scope consistent with the principles and features disclosed herein. In this regard, certain embodiments within the invention may not show every benefit of the invention, considered broadly.

The invention claimed is:

1. A composition comprising, in a cosmetically acceptable medium:
   a mixture of alkanes comprising from 50 to 90% by weight of volatile linear $C_n$ alkane wherein n is from 7 to 15; and from 10 to 50% by weight of volatile linear Cn+x alkane wherein x is greater than or equal to 1, and
   one or more nonprotein cationic polymers selected from a quaternized vinylpyrrolidone/dialkylaminoalkyl acrylate copolymer, a quaternized vinylpyrrolidone/dialkylaminoalkyl methacrylate copolymer; a cellulose ether derivative comprising a quaternary ammonium group; a cationic cyclopolymer; a quaternary polymer of vinylpyrrolidone and vinylimidazole; a crosslinked polymer of methacryloyloxy(C1-C4)alkyltri(C1-C4) alkylammonium salt; and a mixture thereof,
   in a volatile linear alkanes/nonprotein cationic polymer(s) ratio by weight of 1.2 to 20.

2. The composition according to claim 1, wherein the mixture of alkanes comprises at least one of n-heptane (C7), n-octane (C8), n-nonane (C9), n-decane (C10), n-undecane (C11), n-dodecane (C12), n-tridecane (C13), n-tetradecane (C14) or n-pentadecane (C15).

3. The composition according to claim 1, wherein the mixture of alkanes comprises at least one of n-nonane, n-undecane, n-dodecane, n-tridecane or n-tetradecane.

4. The composition according to claim 1, wherein the volatile linear $C_n$ alkane and the volatile linear Cn+x alkane are of vegetable origin.

5. The composition according to claim 1, wherein the mixture of alkanes is present in 0.5 to 90% by weigh with respect to the total weight of the composition.

6. The composition according to claim 1, wherein the one or more nonprotein cationic polymers are present in 0.05 to 10% by weight with respect to the total weight of the composition.

7. The composition according to claim 1, further comprising at least one saturated or unsaturated and linear or branched fatty alcohol comprising from 8 to 32 carbon atoms.

8. The composition according to claim 7, wherein the fatty alcohol is chosen from lauryl alcohol, myristyl alcohol, cetyl alcohol, stearyl alcohol, cetearyl alcohol, oleyl alcohol, behenyl alcohol, hexyldecanol, 2-octyldodecanol and their mixtures.

9. The composition according to claim 7, wherein the fatty alcohol or alcohols are present in 0.1 to 20% by weight with respect to the total weight of the composition.

10. The composition according to claim 1, further comprising at least one fatty ester of a C2-30 mono- or polycarboxylic acid and of a C1-30 mono- or polyalcohol, the total number of carbon atoms in the ester varying from 10 to 50.

11. The composition according to claim 10, wherein the fatty ester or esters are chosen from myristyl myristate, cetyl myristate, stearyl myristate, myristyl palmitate, cetyl palmitate, stearyl palmitate, myristyl stearate, cetyl stearate, stearyl stearate and their mixtures.

12. The composition according to claim 10, wherein the fatty ester or esters are present in 0.1 to 20% by weight with respect to the total weight of the composition.

13. The composition according to claim 1, further comprising at least one silicone.

14. The composition according to claim 1, further comprising at least one additive chosen from ionic or nonionic associative or nonassociative polymers, polyols, proteins, vitamins, reducing agents, plasticizers, softeners, antifoaming agents, moisturizing agents, pigments, clays, inorganic fillers, UV screening agents, inorganic colloids, peptizing agents, solubilizing agents, fragrances, preservatives, anionic, cationic, nonionic or amphoteric surfactants, pearlescent agents, propellants and inorganic or organic thickeners.

15. A method for the treatment of a keratinous substance, comprising applying the composition according to claim 1 to the keratinous substance.

16. The method according to claim 15, wherein the keratinous substance is keratinous fibres.

17. The method according to claim 15, wherein the keratinous substance is hair.

18. The composition according to claim 1, wherein x is from 1 to 2.

* * * * *

UNITED STATES PATENT AND TRADEMARK OFFICE
CERTIFICATE OF CORRECTION

PATENT NO. : 9,095,528 B2
APPLICATION NO. : 12/977227
DATED : August 4, 2015
INVENTOR(S) : Desenne et al.

It is certified that error appears in the above-identified patent and that said Letters Patent is hereby corrected as shown below:

In the claims

Column 20, line 39, claim 5 "weigh" should read --weight--.

Signed and Sealed this
Nineteenth Day of January, 2016

Michelle K. Lee
*Director of the United States Patent and Trademark Office*